United States Patent [19]

Christensen

[11] Patent Number: Plant 5,466

[45] Date of Patent: May 14, 1985

[54] HYBRID TEA ROSE PLANT CV. AROSUMO

[75] Inventor: Jack E. Christensen, Ontario, Calif.

[73] Assignee: Armstrong Nurseries, Inc., Ontario, Calif.

[21] Appl. No.: 651,695

[22] Filed: Sep. 13, 1983

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Synnestvedt & Lechner

[57] ABSTRACT

A new hybrid yellow tea rose for cut flowers and garden decoration having as its seed parent an undisseminated seedling of Camelot × First Prize, and, as its pollen parent "Yankee Doodle". The new cultivar produces well formed yellow flowers in abundant quantities and in contrast to other yellow roses it has a very vigorous growth, is an easy to grow plant and has well above average disease resistance.

1 Drawing Figure

This invention relates to a new class of hybrid tea rose cv. Arosumo. The plant is a hardy, outdoor seedling of the tall, bush type, cultivated for cut flowers and garden decoration. It was propagated by Jack E. Christensen in Ontario, Calif., having as its seed parent an undisseminated seedling of Camelot × First Prize and, as its pollen parent, "Yankee Doodle", U.S. Plant Pat. No. 3,957.

The new rose plant cv. Arosumo is particularly characterized by the following combination of characteristics: its abundant production of well-formed yellow flowers essentially as described and illustrated; its very vigorous growth and easy-to-grow plant which is unusual among yellow roses; its well-above-average disease resistance—also unusual in yellow roses; its well-above-average level of hardiness, lending it well to more severe climates than most yellow Hybrid Teas; its abundant foliage which clothes the entire plant; and its low thorned stems are of suitable length for cutting. It holds the distinguishing characteristics through succeeding propagations by budding.

This new cultivar may be distinguished from its seed plant, an undisseminated seedling of Camelot × First Prize, by the following combination of characteristics:

Arosumo bears flowers of a relatively uniform yellow coloration as described and illustrated, whereas seed parent bears flowers of a relatively uniform light pink coloration.

The seed parent, bears flowers with 20 to 25 petals whereas the flowers of the new cultivar (Arosumo) have significantly higher petalage (37 to 41).

Whereas the seed parent has very large, glossy foliage, the foliage of the new cultivar is smaller and semi-glossy.

Whereas the seed parent produces a bushy plant of medium height, the new rose produces a significantly taller upright bush.

The new cultivar rose (Arosumo) may be distinguished from its pollen parent, "Yankee Doodle"; U.S. Plant Pat. No. 3,957, by the following combination of characteristics:

"Yankee Doodle" bears flowers of a yellow/pink-/orange combination coloration, whereas the new rose bears flowers of a relatively uniform yellow coloration essentially as described and illustrated herein.

Whereas the new rose usually bears flowers with 37 to 41 petals, "Yankee Doodle" bears flowers of a significantly heavier petalage (65 to 75).

The new rose produces a bush with semi-glossy foliage, whereas "Yankee Doodle" produces a bush with glossy foliage.

The new variety usually bears its flowers singly, sometimes two to three flowers per stem and in irregular clusters on normal to strong, long stems for the class. Outdoors, the plant blooms almost continuously and in very abundant quantities during the growing season. It has a slight sweetbriar fragrance.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon The R.H.S. Colour Chart of The Royal Horticultural Society in London, England.

BUD

The peduncle is average length for the class and average to heavy caliper, strong and erect. It is moderately smooth with some stipitate glands and between Yellow-Green 144A and Green 137A in coloration.

Before the calyx breaks, the bud is medium in size for the class, and of medium length, pointed and ovoid in form, with many stipitate glands on the surface of the bud. There are usually slender foliaceous parts extending beyond the tip of the bud equal to one-half or more of its length.

As the calyx breaks, the color is between Yellow-Green 154C and Yellow 2B.

The inner surface of the sepals has a fine, wooly tomentum; margins are lined with stipitate glands and hairs.

As the first petal opens, the bud is average in size for the class, of medium length, pointed ovoid in form. The color on the outside and inside is between Yellow 6D and Yellow 12C with a small basal attachment zone near Yellow 3A. The bud opens up well and is not prevented from opening by hot, wet or dry weather.

BLOOM

The size of the bloom when fully open is average for the class, ranging from $3\frac{1}{2}$ to $4\frac{1}{2}$ inches. The petalage is double, with from 37 to 41 petals and from 3 to 7 petaloids; the petals are arranged regularly. The bloom form when half open is moderately high centered to cupped. The petals are moderately spiraled to cupped with the petal edges moderately reflexed outward. When fully open the bloom is somewhat more loosely cupped with petal edges slightly reflexed outward.

The petals are of heavy substance of medium thickness and with the inside slightly satiny to velvety and the outside slightly shiny. The outside petals are broadly obovate, with a rounded apex. The intermediate petals are nearly round to broadly obovate with a rounded apex. The inside petals are nearly round and with a rounded apex. The colors may be modified by being bordered or shaded or washed or tinted with other colors.

The paragraphs immediately following describe the color values observed in a flower newly opened in the month of July. The plant had been grown outdoors in Ontario, Calif.

The outside and inside surfaces of the outside, intermediate and inner petals have a small basal attachment zone near Yellow 6A and the remainder of the petal quickly suffuses to between Yellow 6C and Yellow-Orange 14C.

The paragraph immediately following describes color values observed in a bloom which had been open for three days, outdoors, in the month of July. The plant had been grown outdoors in Ontario, Calif.

The outside and inside surfaces of the outside and inside petals have a small basal attachment zone near Yellow 6C and the remainder of the petal quickly suffuses to between Yellow 4C and Yellow-Orange 14D.

The general color effect of the newly openend flower is between Yellow 6C and Yellow-Orange 14C. The bloom after being three days open gives a general color effect which is between Yellow 4C and Yellow-Orange 14D. The petals usually drop off cleanly and are not particularly affected by hot, wet or dry weather.

In July, roses grown in the garden last on the bush from 3 to 4 days. Cut roses grown outdoors and kept at living-room temperatures will last from 4 to 5 days in the month of July.

REPRODUCTIVE ORGANS

Many stamens are arranged regularly about the pistils and a few are mixed with petaloids.

The filaments are of a medium to long length. Most are with anthers.

The anthers are of medium to large size and generally open at various times. Their color when immature is near Yellow-Orange 17C and near Orange 26A when mature.

Pollen is moderate to abundant in quantity and near Yellow-Orange 17C in color.

There are an average number of pistils (approximately 55 in number).

The styles are uneven, short to average in length, of thin caliper and somewhat loosely bunched.

The stigma is near Yellow 4B in color.

This variety as grown in Ontario, Calif., does not normally set hips.

FOLIAGE

The compound leaves are borne very abundantly and usually comprise from three to five leaflets. The leaves are of medium to large size for the class, heavy to somewhat leathery and semi-glossy. The leaflets are oval in shape and have an acute apex and a round base. The margin is irregularly serrate.

The mature foliage displays upon its upper surface a color which is between Yellow-Green 147A and Green 139A. The under surface is near Yellow-Green 147B.

The young foliage on its upper surface is between Yellow-Green 146A and Yellow-Green 144A in color and washed heavily with between Greyed-Orange 175A and Greyed Purple 187B. Its under surface is between Yellow-Green 146B and Yellow-Green 144A in color and washed lightly with between Greyed-Orange 175A and Greyed-Purple 187B.

The rachis is of average size, grooved on its upper side, with many stipitate glands on the edges. The under side is sparsely prickly and with stipitate glands.

The stipules are medium to long in length, moderately narrow with medium length points, turning out at an angle usually of less than 45°.

The plant displays a more than average resistance to mildew rust and blackspot compared to other commercial varieties grown under comparable conditions in Ontario, Calif.

GROWTH

The plant is of tall, bushy, upright habit and much branched. It displays a very vigorous growth. The canes are of medium to heavy caliper for the class.

The main stems are between Yellow-Green 146B and Green 139B in color. They bear a few large prickles which are moderately long for the class. They are almost straight and have a medium-length, broad base. The color is near Greyed-Orange 177A. There are a very few small prickles of near Greyed-Orange 177A coloration and no hairs.

The branches are of a color between Yellow-Green 146A and Green 139A. They bear few large prickles, which are of medium to long length for the class. The large prickles are almost straight and have a medium length broad base and a color near Greyed-Yellow 160C. The branches have several small prickles and a few hairs both of a near Greyed-Yellow 160C coloration.

New shoots are between Yellow-Green 146A and Green 143A in color. They bear a few to several large prickles, which are moderately long for the class, almost straight and having a medium-length, broad base and their color is near Yellow-Green 151A. There are many small prickles and many hairs, both near Yellow-Green 151A in color.

I claim:

1. A new and distinct variety of rose plant of the hybrid tea class, substantially as herein shown and described, being particularly characterized in that its abundant production of well formed yellow flowers essentially as described and illustrated; its very vigorous growth; its well-above-average disease resistance; its well-above-average level of hardiness; its abundant foliage which clothes the entire plant and its low-thorned stems that are of suitable length for cutting.

* * * * *

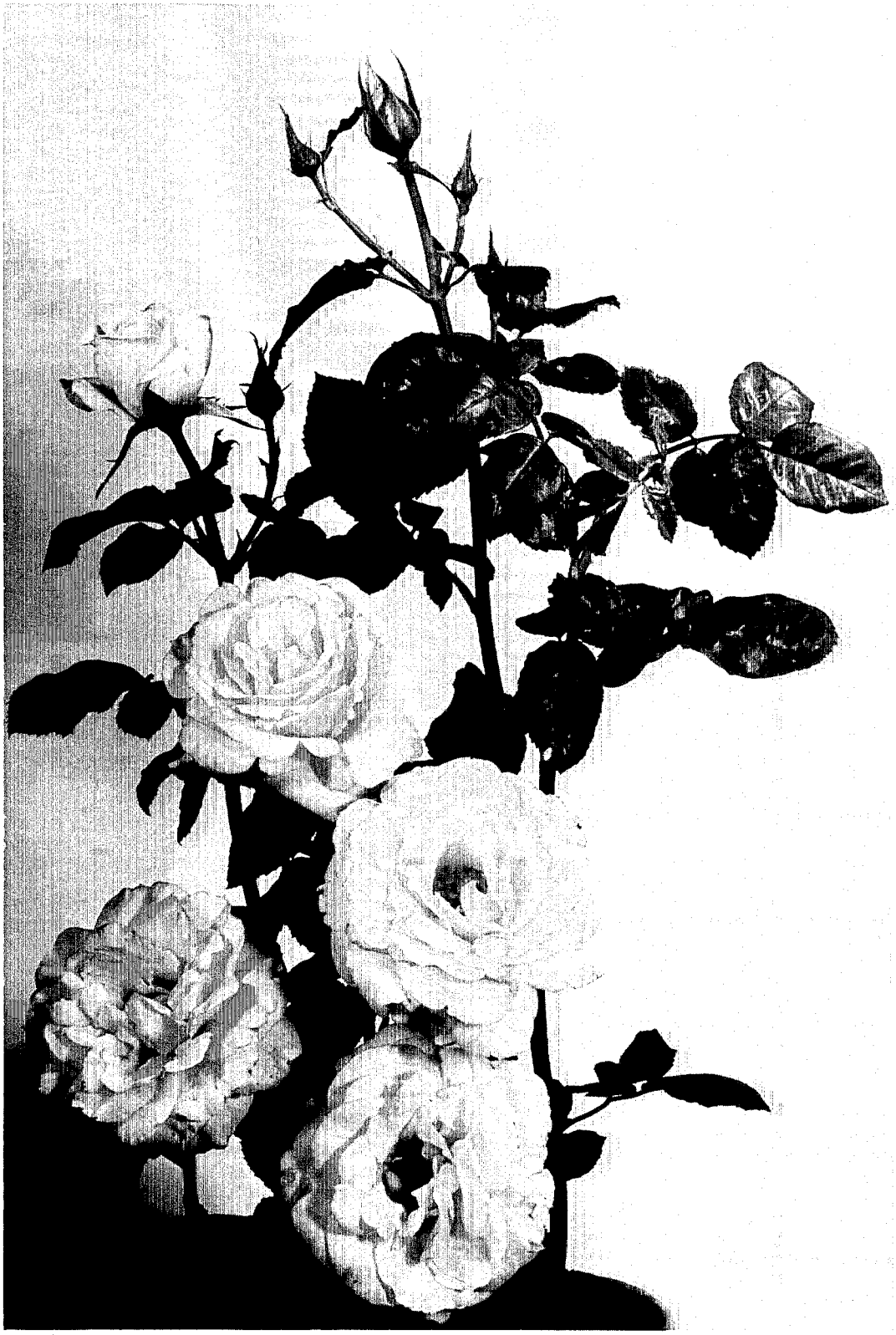

UNITED STATES PATENT AND TRADEMARK OFFICE

CERTIFICATE OF CORRECTION

PATENT NO. : Plant 5,466

DATED : May 14, 1985

INVENTOR(S) : Christensen

It is certified that error appears in the above-identified patent and that said Letters Patent is hereby corrected as shown below:

Cover sheet, serial number: "651,695" should be --531,695--.

Signed and Sealed this

Sixteenth Day of August, 1988

*Attest:*

DONALD J. QUIGG

*Attesting Officer*

*Commissioner of Patents and Trademarks*